(12) United States Patent
Raghukumar et al.

(10) Patent No.: US 7,645,358 B2
(45) Date of Patent: Jan. 12, 2010

(54) PROCESS FOR BIOLOGICAL DEINKING OF OFFICE WASTE PAPER

(75) Inventors: Chandralatha Raghukumar, Goa (IN); C. Mohandass, Goa (IN); Telma Oliviera, Goa (IN); Saeshgiri Raghukumar, Goa (IN); D. Chandramohan, Goa (IN); P. A. Loka Bharathi, Goa (IN); Shanta Nair, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 385 days.

(21) Appl. No.: 11/301,207

(22) Filed: Dec. 12, 2005

(65) Prior Publication Data

US 2006/0260772 A1    Nov. 23, 2006

Related U.S. Application Data (63) Continuation-in-part of application No. 10/103,840, filed on Mar. 25, 2002, now abandoned.

(51) Int. Cl.
*D21C 5/02* (2006.01)

(52) U.S. Cl. ............................. 162/5; 162/72; 510/174

(58) Field of Classification Search .................. 162/4–5, 162/72; 510/174; 435/277–278
See application file for complete search history.

(56) References Cited

U.S. PATENT DOCUMENTS

| | | | |
|---|---|---|---|
| 5,318,905 A * | 6/1994 | Saito et al. | 435/209 |
| 5,525,193 A * | 6/1996 | Franks et al. | 162/5 |
| 5,582,681 A * | 12/1996 | Back et al. | 162/5 |
| 5,620,565 A * | 4/1997 | Lazorisak et al. | 162/72 |
| 6,022,423 A | 2/2000 | Bhatia | |
| 6,027,610 A * | 2/2000 | Back et al. | 162/111 |
| 6,391,150 B1 * | 5/2002 | Berger et al. | 162/4 |
| 6,426,200 B1 * | 7/2002 | Yang et al. | 435/72 |
| 6,576,083 B2 * | 6/2003 | Franks et al. | 162/5 |
| 6,767,728 B2 * | 7/2004 | Yang et al. | 435/207 |
| 7,138,261 B2 * | 11/2006 | Nakane et al. | 435/200 |
| 7,297,224 B2 * | 11/2007 | Nakamura et al. | 162/5 |
| 7,374,921 B2 * | 5/2008 | Okakura et al. | 435/209 |
| 2002/0142452 A1 * | 10/2002 | Yang et al. | 435/278 |
| 2002/0179261 A1 * | 12/2002 | Franks et al. | 162/5 |
| 2003/0178162 A1 * | 9/2003 | Raghukumar et al. | 162/5 |
| 2004/0016522 A1 * | 1/2004 | Franks et al. | 162/4 |
| 2004/0038841 A1 * | 2/2004 | Koga et al. | 510/226 |
| 2005/0039869 A1 * | 2/2005 | Franks et al. | 162/5 |
| 2005/0102762 A1 * | 5/2005 | Nakane et al. | 8/115.51 |
| 2005/0121156 A1 * | 6/2005 | Nakamura et al. | 162/5 |
| 2006/0035361 A1 * | 2/2006 | Okakura et al. | 435/200 |
| 2006/0124266 A1 * | 6/2006 | Xu et al. | 162/199 |
| 2006/0154843 A1 * | 7/2006 | Wang et al. | 510/320 |
| 2006/0210971 A1 * | 9/2006 | Kerovuo et al. | 435/6 |
| 2006/0260772 A1 * | 11/2006 | Raghukumar et al. | 162/5 |
| 2008/0073042 A1 * | 3/2008 | Chandralata et al. | 162/5 |

FOREIGN PATENT DOCUMENTS

| | | |
|---|---|---|
| EP | 717144 | 6/1996 |
| GB | 2304741 | 3/1997 |
| JP | 2160984 | 6/1990 |
| JP | 3000882 | 1/1991 |
| JP | 06346390 | 12/1994 |
| JP | 10313859 | 12/1998 |
| KR | 9303705 | 5/1993 |
| WO | WO 2007017889 A1 * | 2/2007 |

OTHER PUBLICATIONS

Gleisner et al. "Industrial review: Semiannual Patents Review; Jul.-Dec. 2003," May 2004, Progress in Paper Recycling, vol. 13, No. 3, pp. 34-42.*
Chemical Coatings Engineering, Ink Composition in Ink Jet Printers, from Internet, www.eng-tips.com/gviewthread.cfm/lev2/7/lev3/40/pid/116/qid/6661, Dec. 2001.
Thomas W. Jeffries, "Enzyme Technology for Pulp Bleaching and Deinking", Sep. 26, 1996, 9 pages, http://calvin.biotech.wisc.edu/jeffries/enztech/enztech_toc.html.

* cited by examiner

*Primary Examiner*—José A Fortuna
(74) *Attorney, Agent, or Firm*—Butzel Long (57) ABSTRACT

This invention relates to a biological process for deinking of office waste paper, and more particularly the present invention relates to a biological process for deinking of xerographic and inkjet printed paper using a gram-negative coccoid bacterium deposited at the National Institute of Oceanography, Dona Paula, Goa 403 043, India having Accession No. NIO/DI/32 and being deposited at the Agricultural Research Cultural Collection, and International Depository, having Accession Number NRRL B-30638.

20 Claims, 9 Drawing Sheets

PROCESS FOR BIOLOGICAL DEINKING OF OFFICE WASTE PAPER

CROSS-REFERENCE TO RELATED APPLICATION

This application is a continuation-in-part of U.S. Ser. No. 10/103,840, filed Mar. 25, 2002 now abandoned.

FIELD OF THE INVENTION

The present invention relates to decolorization of office waste paper using microorganisms from marine habitats. More particularly, the present invention relates to a process for biological deinking of photocopied and inkjet-printed paper or toner photocopied paper pulp using a gram-negative coccoid bacterium deposited at National Institute of Oceanography, Dona Paula, Goa 403 043, India having Accession No. NIO/DI/32 and being deposited at the Agricultural Research Cultural Collection, and International Depository, having Accession Number NRRL B-30638.

BACKGROUND OF THE INVENTION

Paper manufacturing is a major industry and a continuously growing one. Increased production of paper imposes a severe demand on plant raw material and thus harms the environment. Recycling of used paper is an alternative that can alleviate the stress that is exercised on the environment. The three major sources of raw material for such recycling are newsprint, photocopied paper and inkjet-printed papers. Recycling of paper requires the removal of the printing ink from the used paper, called deinking, so that the processed material is brighter. Printing on paper is accomplished by using two types of inks, the impact and the non-impact inks. In impact inks, used for newsprints, the ink does not fuse with the paper and is, therefore, easy to remove or disperse during the deinking, or recycling process. Such recycling is now well known and has been carried out for years. On the contrary, non-impact inks used in photocopying, ink-jet printing and laser printing results in the ink fusing with the paper and makes it non-dispersible, thus rendering the deinking process much more difficult (Jeffries, 2002). The toners used for photocopying generally contain iron oxide (about 55%0, olefins (about 5%) and plastic or polymer (Website:http://www.eng-tips.com).

Various hydrolytic enzymes such as cellulase, lipase, amylase of bacterial or fungal origin, individually or in combination have been used for deinking of office waste paper.

(i) A reference may be made to a publication wherein, a method for deinking of xerographic and printed paper, collectively called office waste, includes applying deinking solution to the paper to be deinked, the deinking solution being composed of a cleaning solution and a surfactant, abrading the paper to remove the ink from paper, and washing the paper to remove the deinking solution from the paper (U.S. Pat. No. 6,022,423 Bhatia, S. 1996 Method for deinking paper dated 2000-2, Aug.). However, this patent involves using a special device for deinking of whole sheets and cannot be used on pulp.

(ii) Another reference may be made to wherein, a monocomponent cellulase is used for removal of ink and toners from printed paper (U.S. Pat. No. 5,525,193 Neal, E., Steven, B. E., Hans, H. C. 1994. Use of monocomponent cellulase for removing inks, coatings and toners from printed paper). The technique of isolating monocomponent cellulase from microorganisms by various purifications, chromatographic steps is time consuming and expensive.

(iii) A reference may be made to a publication wherein, endogluconases and hemicellulases from several fungi are used effectively for deinking of Xerox and laser-printed paper (Gubitz, G. M., Mansfield, S. D., Bohm, D. Saddler, J. N. 1998. Effect of endoglucanases and hemicellulases in magnetic and flotation deinking of xerographic and laser-printed papers. Journal of Biotechnology. 65:209-215). As mentioned above the enzyme technology is still an expensive one for using on a large scale.

(iv) A reference may be made to a publication, wherein deinking of laser printed or xerographic paper is done using enzyme containing a resistant binder. Enzyme is added in the specified form to improve speck removal (Landley, J. G. Stockwell, J. O. 1997. Enzyme deinking of paper. Patent Number GB 2304741 dated 26 Mar. 1997). As with the above references, the technology to produce enzymes, their purification and application is an expensive process.

(v) A reference may be made to a publication, wherein deinking of office waste paper is carried out by contacting the pulp with a deinking agent containing enzymes cellulase, preferably active at pH 4 to 8. The treated paper is used in the production of newsprint and high quality paper (Jobbins, J. M. Asbrand, Jr. G. R. 1996. Composition and process for deinking office waste paper. Patent Number EP 717144 dated 19 Jun. 1996). As with the above references, the technology to produce enzymes, their purification and application is an expensive process.

(vi) A reference may be made to a publication, wherein deinking of waste paper is achieved by incubating the paper pulp with cellulase at 40° C. for 1 hour under pressure. Following dissociation of ink particles, the resulting washed pulp is brighter (Mitsubishi Heavy Industries. 1994. Deinking of waste paper. Patent number JP06346390 dated 20 Dec. 1994). As with the above references, the technology to produce enzymes, their purification and application is an expensive process.

(vii) A reference may be made to a publication, wherein deinking is achieved by using lipase to remove ink from used paper. The procedure is carried out under neutral or alkaline conditions which produces regenerated pulp having enhanced brightness (Novo. 1990. Removing ink from used paper. Patent number JP2160984 dated 20 Jun. 1990).

(viii) A reference may be made to a publication, wherein deinking of waste paper is done by using the yeast *Hansenula polymorpha*, which degrades the ink-based resin (Jeonju-Paper. 1993. Waste-paper deinking. Patent Number KR 9303705 dated 8 May 1993). However, the ink floats on the surface and the pulp has to be extensively washed to remove the detached ink.

(ix) A reference may be made to a publication, wherein decolorization of Indian ink is achieved by using thermostable alkaline cellulase from a *Bacillus* sp (Kao. 1998. A microbiologically produced thermostable alkaline cellulase and a process for its preparation. Patent number JP10313859).

OBJECTS OF THE PRESENT INVENTION

The main object of the present invention is to provide a process for decolorization of waste paper.

Another object of the present invention is to provide a process for biological deinking of photocopied and inkjet-printed paper pulp using a gram-negative coccoid bacterium deposited at National Institute of Oceanography, Dona Paula, Goa 403 043, India, having Accession No. NIO/DI/32, and being deposited at the Agricultural Research Service Cultural Collection, an International Depository, 1815 N. University Street, Peoria, Ill. (USA) 61604, and having Accession Number NRRLB-30638.

SUMMARY OF THE INVENTION

The present invention provides a process for decolorization of paper pulp and more particularly, the present invention relates to a process for biological deinking of photocopied and inkjet-printed paper pulp using a gram negative coccoid bacteria deposited at National Institute of Oceanography, Dona Paula, Goa 403 043, India having accession No. NIO/DI/32 and being deposited at National Institute of Oceanography, Dona Paula, Goa 403 043, India having Accession No. NIO/DI/32 and being deposited at the Agricultural Research Cultural Collection, and International Depository, having Accession Number NRRL B-30638.

Brief Description of Accompanying Drawings In the drawings accompanying the specification.

The present invention is further described with reference to the accompanying examples, which are given by way of illustration and therefore, should not be construed to limit the scope of the present invention in any manner.

DETAILED DESCRIPTION OF THE PRESENT INVENTION

Accordingly, the present invention provides a process for biological deinking of office waste paper inclusive of xerographic and inkjet-printed paper printed with non-impact and non-dispersible ink, said process comprises:

(a) growing coccoid bacterial isolate deposited at National Institute of Oceanography, Dona Paula, Goa 403 043, India having accession No. NIO/DI/32 and being deposited at National Institute of Oceanography, Dona Paula, Goa 403 043, India having Accession No. NIO/DI/32 and being deposited at the Agricultural Research Cultural Collection, and International Depository, having Accession Number NRRL B-30638, in a nutrient broth containing beef extract, peptic digest of animal tissue and salinity ranging between 30 to 35 parts per thousand for at least 4 days;

(b) adding the resulting biomass of step (a) at 20% concentration to inoculate paper pulp diluted to at least 6% consistency suspended in sea water with salinity diluted to 50%;

(c) incubating the inoculated pulp for a minimum period of 96 hours followed by diluting the pulp tenfold;

(d) adding 1% by wt. of a surfactant and aerating for at least 10 minutes with compressed air to let the stray residual ink particles and contaminants flow out of the container, and (e) filtering the pulp of step (d) over a funnel under suction, to get a sheet of pulp with uniform thickness and reading the brightness by radiance measurement.

In an embodiment of the present invention, wherein in step (a), the bacterium is grown for a minimum of 4 days in nutrient broth containing beef extract and peptic digest of animal tissue in sea water with salinity diluted to 50%.

In another embodiment of the present invention, wherein in step (b), the resulting bacterial biomass is concentrated by centrifugation and diluted to get final optical density of 1.0 measured at 600 nm in a spectrophotometer.

In yet another embodiment of the present invention, the diluted bacterial culture is inoculated to at least 6% pulp suspended in seawater with salinity diluted to 50% and incubated for a minimum period of 4 days within to completely bleach the pulp.

In still another embodiment of the present invention, the resulting deinked pulp is diluted tenfold, to which 1% surfactant is added, aerated using compressed air, and any free residual ink particles and contaminants are allowed to flow out of the solution.

In a further embodiment of the present invention, wherein after step (d) the xerographic or inkjet-printed paper is soaked in hot water for 1-2 hours and macerated after adding 1% surfactant to pulp.

In one more embodiment of the present invention, the paper is macerated using conventional mixers.

In one another embodiment of the present invention, wherein in step (e), the washed pulp is filtered over a Buchner funnel under suction to get a pulp sheet of uniform thickness.

In an embodiment of the present invention, the pulp sheet is pressed at 60° C. for a minimum of 4-5 hours to make it uniform and dried.

In another embodiment of the present invention, the radiance of the resultant sheet is read from 412 to 684 nm and the radiance expressed as Lux units (LU) {wherein one LU is equivalent to $\mu W/cm^2/nm/Sr$}.

In still another embodiment of the present invention, the pulp sheet made out of recycled paper is used as a reference.

In yet another embodiment of the present invention, wherein in steps (a) and (b), pure water containing 1.5% by wt of sodium chloride can be used in the place of sea water.

Deinking of paper is a limiting factor in recycling of paper. Newsprint and office waste paper is generally deinked using chemicals which go into the effluent and cause pollution of the water bodies. The newsprint or offset printing is done using dispersible or non-impact ink whereas laser, xerographic and ink-jet printer ink does not disperse and is also called impact ink. There are several papers describing various methods of deinking by using hydrolytic enzymes such as cellulase, hemicellulase and lipase of microbial origin which release toner particles from fibers. However, enzyme action is affected by the paper constituents in the deinking condition. The chemically pulped fibers are more susceptible than mechanically pulped fibers. Office waste paper is high in laser and toner content and the technology for taking the toner particles out is not very good at the moment (Jefferies, 2002).

In the present invention, Applicants report a process for deinking of office waste paper comprising xenographic and ink-jet printed paper by a bacterium isolated from marine sediment of an estuary in Goa, India. The salinity of the water at the time of isolation was around 15 parts per thousand, which is equivalent to half-strength sea water.

The present invention provides a process for biological deinking of office waste paper comprising xerographed, ink-jet printed, and similar other non-impact ink printed papers. The process is achieved by using a coccoid bacterium deposited at National Institute of Oceanography, Dona Paula, Goa 403 043, India having Accession No. NIO/DI/32 and being deposited at National Institute of Oceanography, Dona Paula, Goa 403 043, India having Accession No. NIO/DI/32 and being deposited at the Agricultural Research Cultural Collection, and International Depository, having Accession Number NRRL B-30638, said culture may be grown in nutrient broth containing beef extract, and peptic digest of animal tissue and prepared with sea water with its salinity diluted to 50%.

The present invention more particularly provides a process wherein the aforesaid pre-grown bacterial culture is inoculated on the office pulp suspended in seawater with its salinity diluted to 50% and incubated for a minimum period of 4 days to decolorize the paper pulp.

The paper pulp becomes brighter, the black ink is totally decolorized and the supernatant water remains clear. The water needs to be simply drained to recover the deinked pulp. The pulp can be diluted tenfold optionally to remove any free residual ink particles and other contaminants. Conventional surfactant at 1% concentration may be added to the diluted paper pulp, aerated for at least 10 minutes by which the particles float and go out of the pulp slurry. The washed pulp can be filtered over a large funnel under suction and dried at 60° C. for at least 6 hours to obtain decolorized paper pulp.

The organism given in the present invention is a gram-negative, coccoid bacterium isolated from coastal marine sediment. The coccoid bacterium has been deposited at National Institute of Oceanography, Dona Paula, Goa 403 043, India having Accession No. NIO/DI/32 and being deposited at the Agricultural Research Cultural Collection, and International Depository, having Accession Number NRRL B-30638. Said bacterium can be grown in nutrient broth containing beef extract, peptic digest of animal tissue, prepared with sea water with salinity diluted to 50% and having a pH of at least 7.5. The bacterium when grown in nutrient agar medium appears as circular colonies off-white in color, having 2 mm diameter colonies in the beginning and growing to a size of 5 mm within 3-4 days. The bacterium is capable of producing lipase and amylase in the presence of Tween 80 and starch respectively. It is fermentative and catalase-negative bacterium. The bacterium is grown at room temperature (30° C.) for about 4 days, the bacterial cells are collected by centrifugation under sterile conditions, diluted appropriately to get optical density of 1 at 660 nm. Xerographic, ink-jet printed paper and other papers having printed with impact ink are pulped by soaking in hot water for a minimum of 2 hrs, macerated in a domestic mixer with surfactant such as Tween 80. An example for the process for deinking involves suspending such a pulp at least at 6% consistency in seawater with salinity diluted to 50%, inoculating with 20% bacterial suspension prepared as described above and incubating at room temperature for a minimum of 4 days to get completely decolorized pulp and the ink is disappeared from water also. The pulp can be diluted, aerated from bottom to remove free contaminating particles, salts and bacterial cells. A surfactant such as Tween 80 can be added at 1% concentration for flotation of any residual ink particles. The pulp is filtered over a Buchner funnel under suction, pressed with flat stainless steel plates to make the pulp sheet uniform in thickness. The radiance of the resultant sheet is read from 412 to 684 nm and the radiance expressed in Lux units (Lu). One LU is equivalent to $\mu W/Cm^2/nm/Sr$. The ratio of radiance between recycled paper purchased from the market and biologically deinked paper is taken as a measure of brightness.

In a typical example plain toner powder of Xerox machine suspended in seawater with its salinity diluted to 50% also became completely colorless within 7 days after inoculating it with the said bacterial suspension.

Most of the organisms used for biological deinking release ink particles from the fibers and they need to be subsequently washed off from the pulp. In the process described in the present invention, this problem does not arise as the ink and toner particles are totally decolorized. The method is very cost effective as the only step involved is raising the bacterial inoculum in any conventional nutrient broth containing assimilable carbon and nitrogen source. A comparative statement given in Table 1 explains the novelty of our invention in comparison with prior art known in this field.

TABLE 1

Comparative statement

| Reference (Prior art) | Type of paper or ink | Source of deinking agent | Remarks |
| --- | --- | --- | --- |
| Patent U.S. Pat. No. 6,022,423 | Impact ink and office waste | Chemical & a surfactant, abrading the paper and washing the deinked paper using a special device to put whole sheet | Not practical on a large scale |
| U.S. Pat. No. 5,525,193 | Toner, impact ink from mixed office waste | Monocomponent cellulase purified from cellulytic enzymes of various microorganisms or genetically engineered organism which produces only monocomponent cellulase | Enzyme technology is expensive |
| Gubitz et al. 1998 | Xerox and laser-printed paper | Endogluconases and hemicellulases from fungi | Enzyme technology is expensive. |
| GB2304741 | Laser-printed or xerographic paper | Enzyme containing a resistant binder | Purification and application of enzyme technology is still expensive |
| Patent EP 717144 | Office waste paper | Cellulase | Expensive enzyme technology |
| JP06346390 | Office waste paper | Contacting with cellulase at 40° C. for 1 h under pressure | Enzyme high temperature and pressure will make the cost of technology not very practical. |
| JP2160984 | Office waste paper | Contacting pulp with lipase enzyme under neutral or alkaline conditions | Adjustment of Ph and enzyme technology will not make it very practical. |
| KR 9303705 | Office waste paper | Contacting pulp with the culture of the yeast Hansenula polymorpha which degrades the ink-based resin. | The ink floats on the surface and the pulp has to be extensively washed |
| JP10313859 | For decolorization of Indian ink | Thermostable alkaline cellulase from a bacterium | Recommended for surfactant composition, as a fiber treatment agent and as an Indian ink decolorization agent. |
| Our invention | For Xerox and inkjet-printed paper pulp | Direct contact of pulp slurry with the bacterium NIO/DI/32 for 72 h to get complete decolorization of the pulp and clear water | No enzyme, no temperature or Ph adjustment, the pulp and the water are clear and washing is only optional. |

EXAMPLE 1

The bacterial isolate NIO/DI/32 was isolated from the coastal esturine sediment, Dona Paula, Goa, India in nutrient agar medium containing beef extract and peptic digest of animal tissue and agar in sea water with its salinity diluted to 50%. The culture was maintained in the slants of nutrient agar medium for all further experiments.

The said bacterium can be grown in nutrient broth containing beef extract, peptic digest of animal tissue in sea water with its salinity diluted to 50%. The bacterium is grown at room temperature (30° C.) for about 4 days, the bacterial cells are collected by centrifugation under sterile conditions, diluted appropriately to get optical density of 1 at 660 nm using a spectrophotometer. Xerographic paper printed with impact ink from HP machine are pulped by soaking in hot water for a minimum of 2 hrs, macerated in a conventional domestic mixer with surfactant such as Tween 80. An example for the process for deinking involves suspending such a pulp at least at 6% consistency (6 g wet pulp in 100 ml of water) in sea water with its salinity diluted to 50%, inoculating with 20% bacterial suspension prepared as described above and incubating at room temperature for a minimum of 4 days to get completely deinked pulp with the ink totally disappearing from the supernatant water. The pulp can be diluted, aerated from bottom to remove free contaminating particles, salts and bacterial cells. A surfactant such as Tween 80 can be added at 1% concentration for flotation of any residual ink particles. The pulp is filtered over a Buchner funnel under suction, pressed with flat stainless steel plates to make the pulp sheet uniform in thickness. The radiance of the resultant sheet is read from 412 to 684 nm and the radiance expressed in Lux units (Lu). One Lu is equivalent to $\mu W/cm^2/nm/Sr$. The ratio of radiance between recycled paper available in any stationary shop and biologically deinked paper is taken as a measure of brightness.

Figure 1:
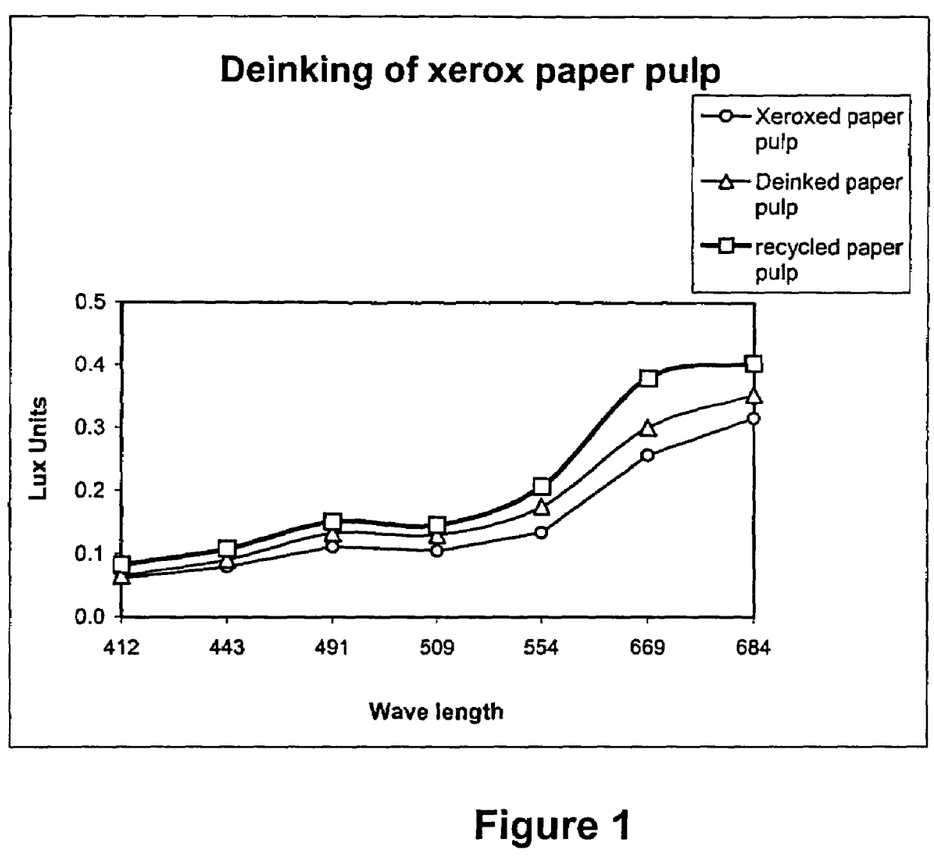
FIG. 1 shows the radiance of Xerox paper pulp (XP) is lowest in comparison with that of recycled paper pulp (RP) and biologically deinked pulp (BP)
Figure 2:
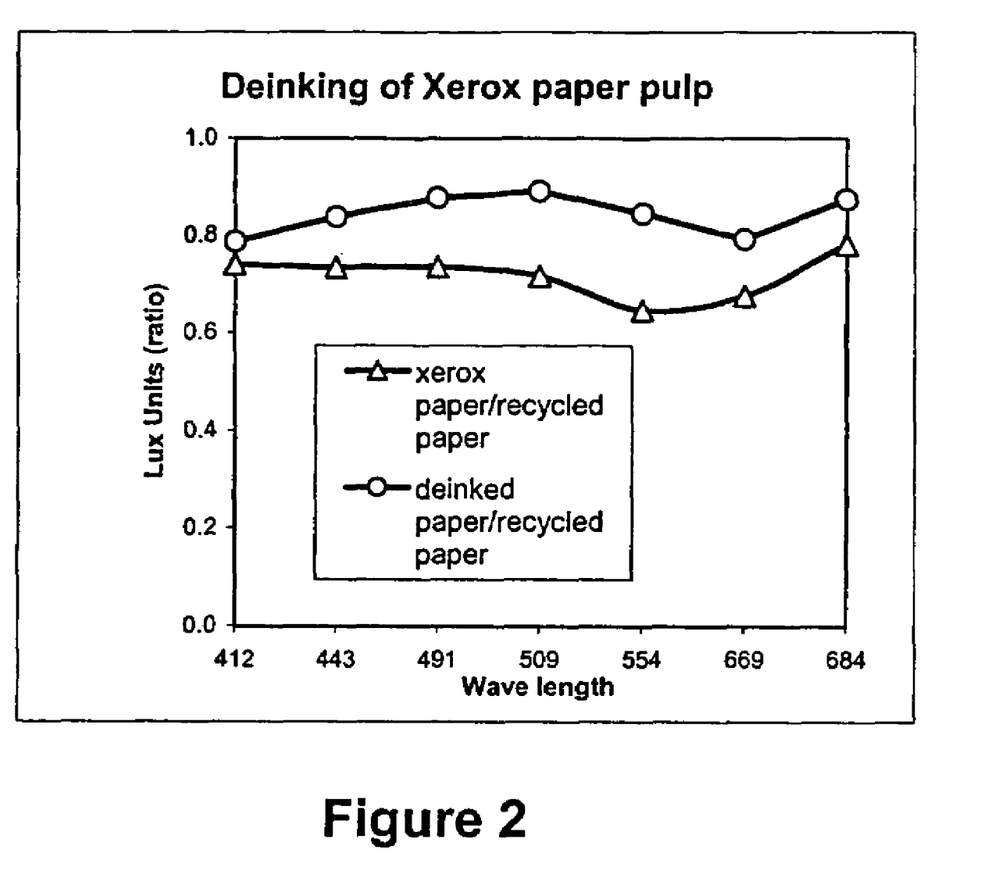
FIG. 2 shows the ratio of radiance of biologically deinked paper to that of recycled paper.

Accordingly, FIG. 1 shows the radiance of Xerox paper pulp (XP) is lowest in comparison with that of recycled paper pulp (RP) and biologically deinked pulp (BP). This brightness was achieved 4 days after inoculation with the said bacterium. As the target was to achieve brightness of recycled paper, the Applicants have shown the same data as ratio of radiance of Xerox paper to recycled paper and similarly, the ratio of radiance of biologically deinked paper to that of recycled paper is shown in FIG. 2.

Figure 3:
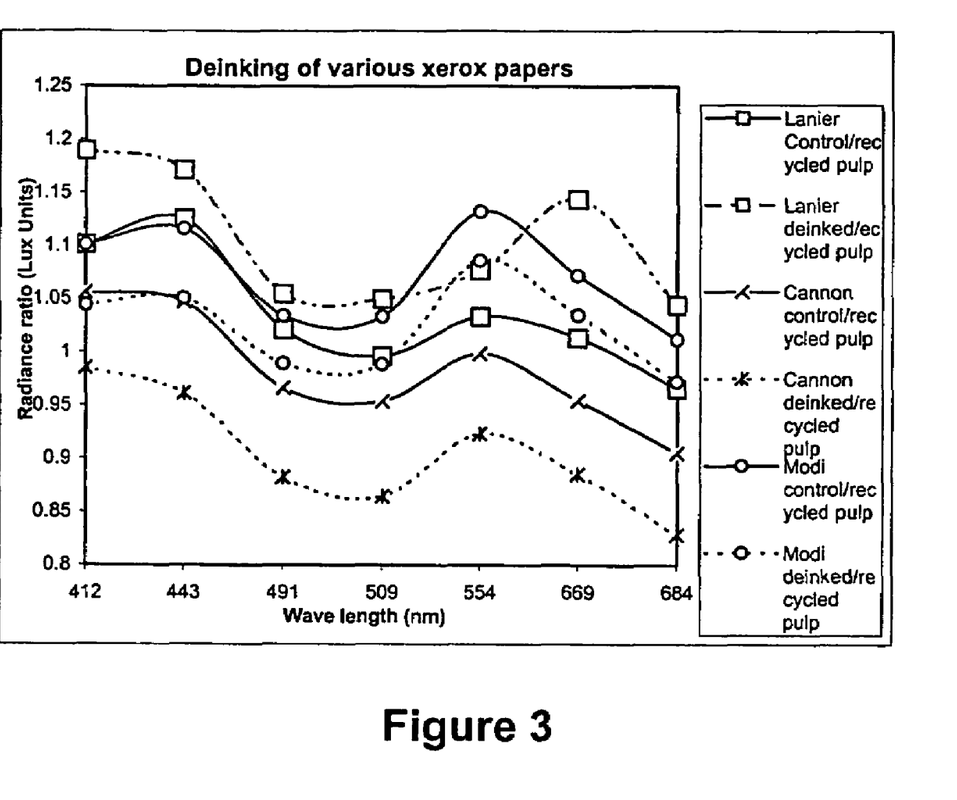
FIG. 3 compares the deinking done by the present invention on papers of three different photocopier machines.

Xerographic printed paper obtained from various Xerox machines were compared for their efficiency in being deinked by the said bacterium. Accordingly FIG. 3 shows that out of 3 different machines, Xerox paper obtained from Lanier machine were deinked effectively by the process described in the present invention.

EXAMPLE 2

As seen in the previous example, the bacterium could grow in the plain paper pulp suspended in water, and bleach the pulp in 4 days, the Xerox toner (HP make) at 1% concentration was suspended in sterile sea water and inoculated with the said bacterial suspension and incubated at room temperature for 15 days. The control flask did not receive any bacterial inoculum. The contents of experimental flask and the control flask did not receive any bacterial inoculum. The contents of experimental flask and the control flask were filtered over pre-weighed filter paper, rinsed with sterile distilled water to remove salts and dried to a constant weight at 60° C. The difference in weight of residual toner powder was compared in the two sets.

Accordingly, in the experimental flask after 15 days the dry weight was 143 mg whereas, in the control flask it was 220 mg. Thus, almost 65% toner was degraded in the inoculated flasks. Besides, the water in the experimental flask became almost colorless.

EXAMPLE 3

The ability of the bacterial isolate having Accession Number NIO/DI/32 (also being deposited at an international depository) to deink ink-jet printed paper was tried as follows:

The inkjet-printed paper was prepared into pulp as described in Example 1 and inoculated with the said bacterium as described in Example 1. However, the inoculum dose varied from 2 ml to 10 ml with the increment of 2 ml. The other procedures used were the same as described in the Example 1.

Figure 4:
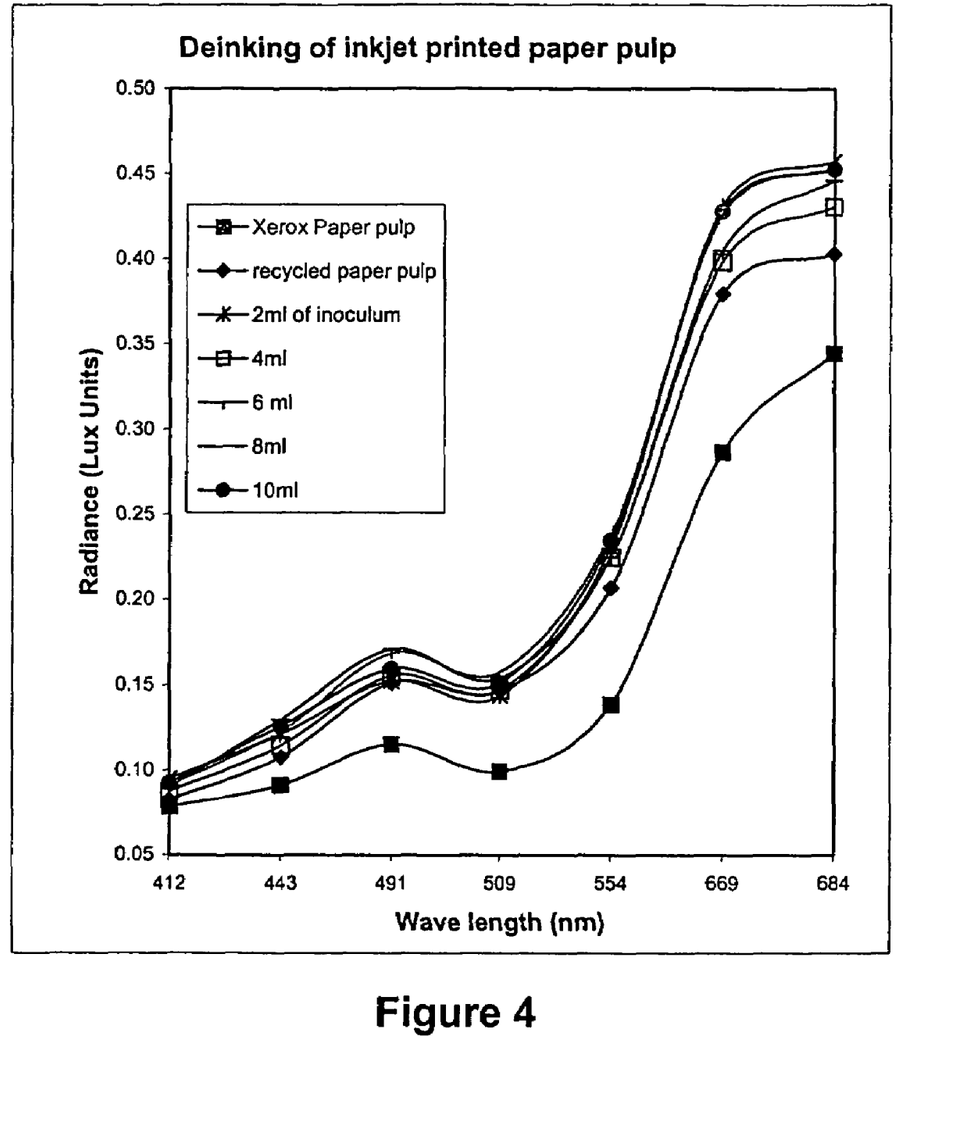
FIG. 4 compares the radiance of decolorized paper pulp after 4 days at different concentration of inoculum.

Accordingly, FIG. 4 shows radiance of decolorized paper pulp after 4 days in comparison with Xerox and recycled paper. The radiance of biologically deinked paper was more than the recycled paper and there was not much difference between inoculum concentration of 6 to 10 ml in the final radiance achieved.

Figure 5:
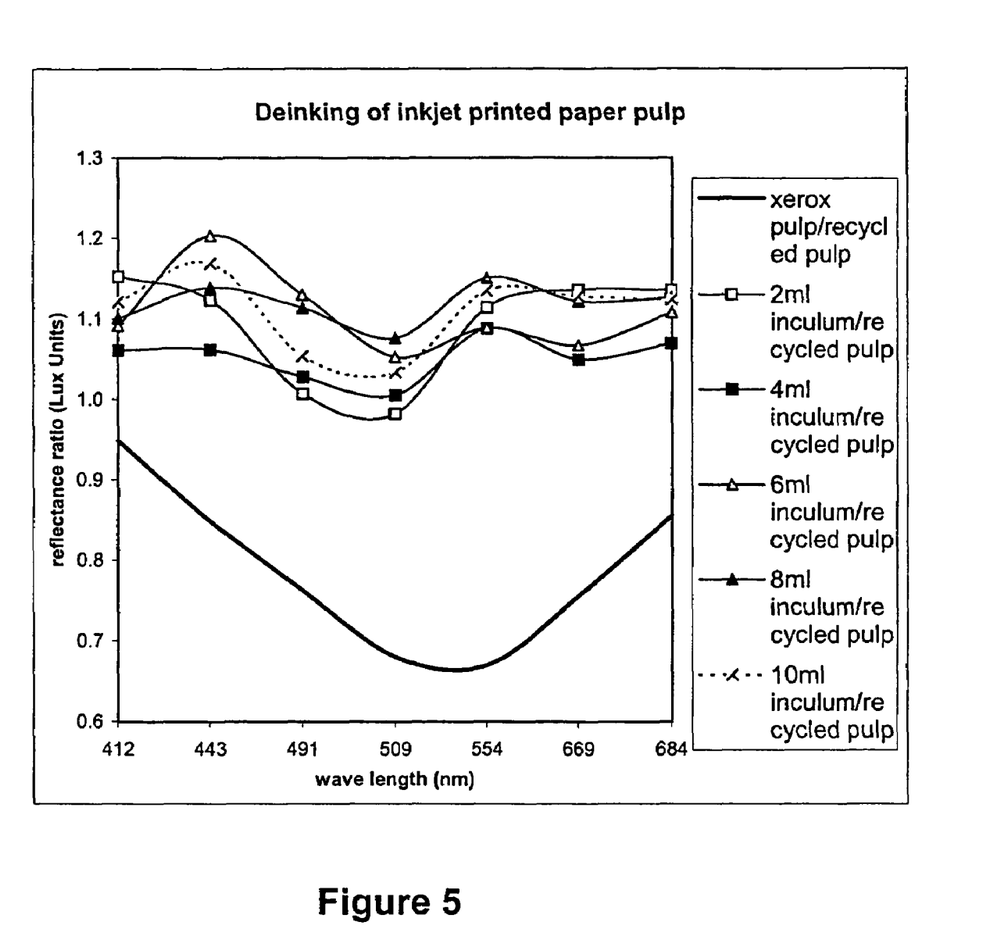
FIG. 5 compares the reflectance ratio of the deinked paper pulp at different concentrations of inoculum.

FIG. 5 shows the ratio of reflectance between Xerox paper to recycled paper in comparison with paper pulp deinked using different concentrations of the said bacterial suspension. The brightness achieved by using 8 ml or 10 ml inoculum was almost similar.

EXAMPLE 4

The deinking of inkjet-printed paper in relation to time of incubation (in days) was carried out as follows:

The preparation of pulp, inoculum and experimental set up were the same as in the previous example, but the inoculum concentration used here was 10 ml and radiance of the pulp was tested on day 2, 4, 6 and 8 days after incubating the pulp with the said bacterial culture.

Figure 6:
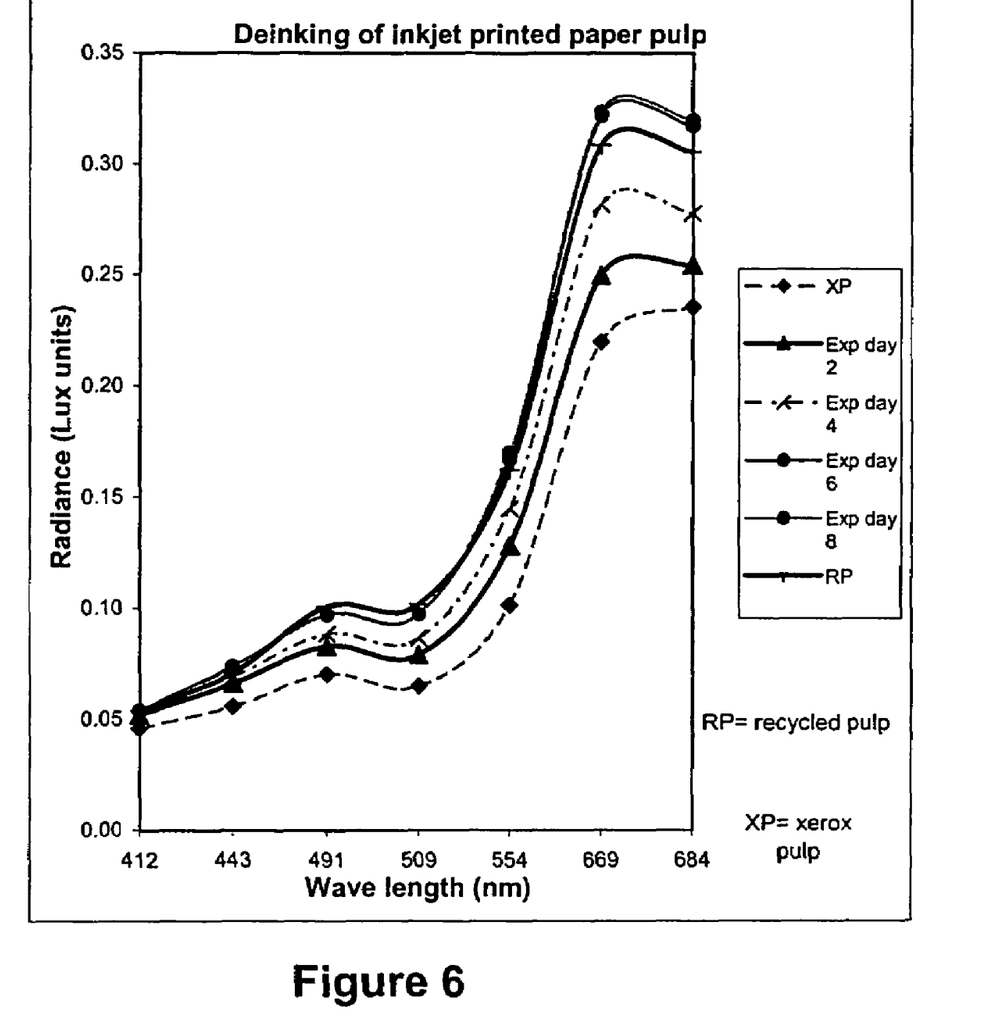
FIG. 6 compares the radiance ratio of the deinked paper pulp with the number of days.

According, FIG. 6 shows that by day 6 maximum brightness is achieved and here also the radiance of biologically deinked pulp was slightly greater than that of recycled paper purchased from the market. The control was the inkjet-printed paper pulp.

Figure 7:
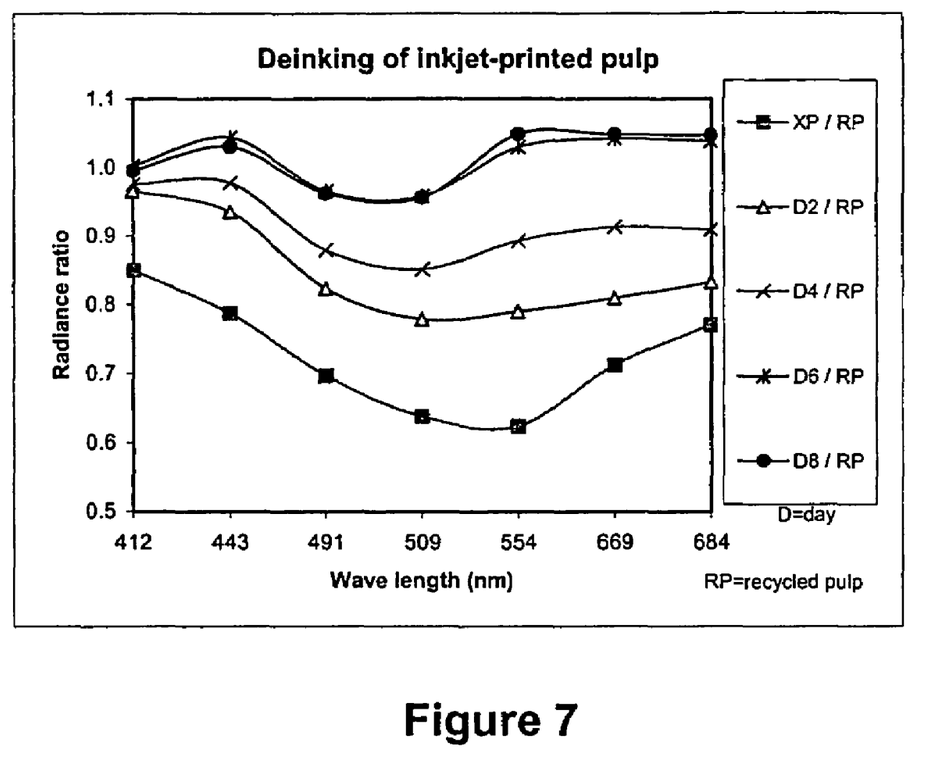
FIG. 7 shoes the ratio of radiance between recycled paper and deinked paper.

FIG. 7 shows the ratio of radiance between recycled paper and deinked paper. The control was the inkjet-printed paper pulp which showed lowest radiance ratio.

EXAMPLE 5

Ability of the said bacterium to deink the inkjet-printed paper with two concentrations of the inoculum at varying incubation period was compared to arrive at a combination where deinking is achieved in a shortest time.

Figure 8:
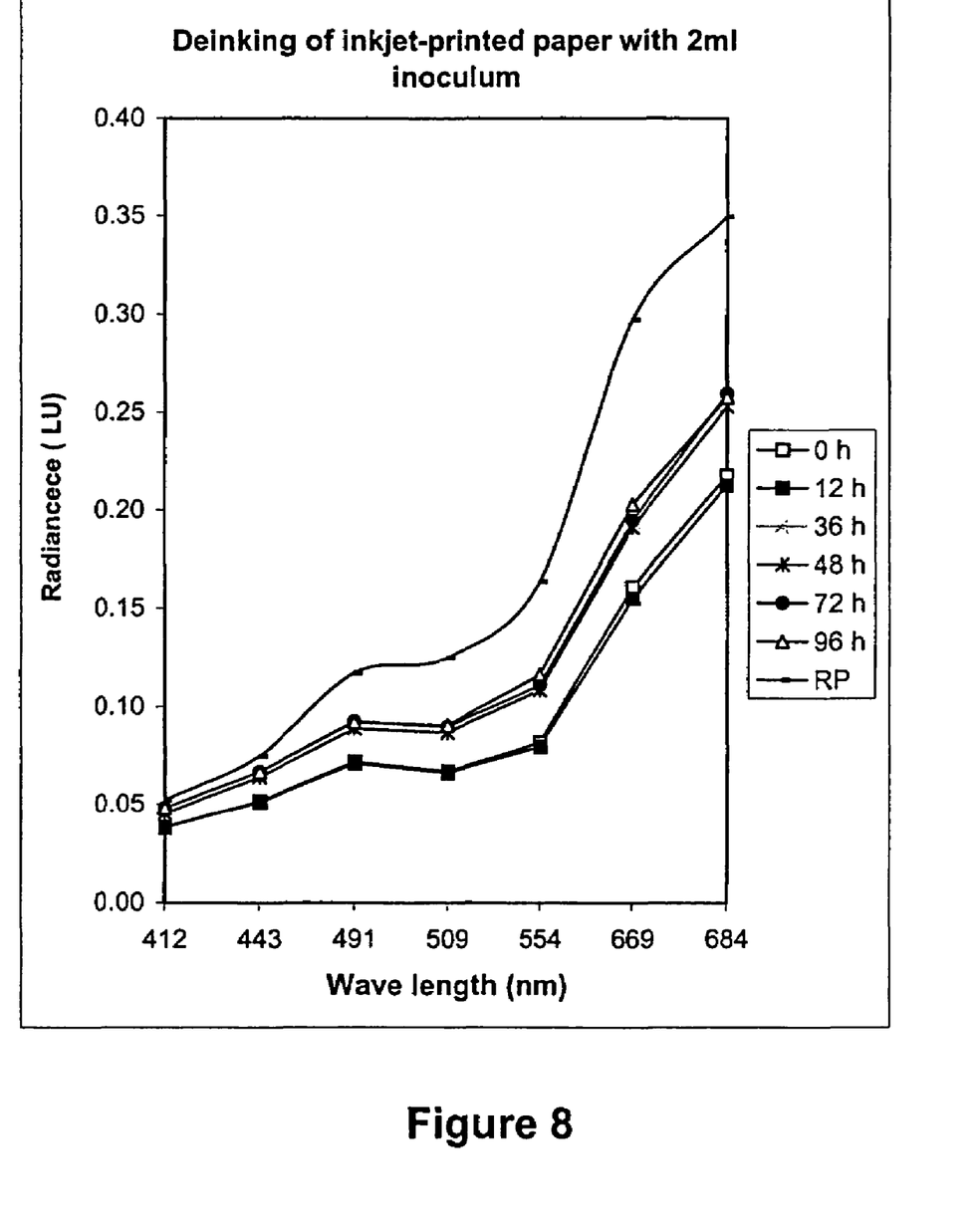
FIG. 8 shows that with an inoculum concentration of 2 ml, maximum brightness is achieved after 72 hours.

Accordingly, FIG. 8 shows that with an inoculum concentration of 2 ml, maximum brightness is achieved after 72 hours.

Figure 9:
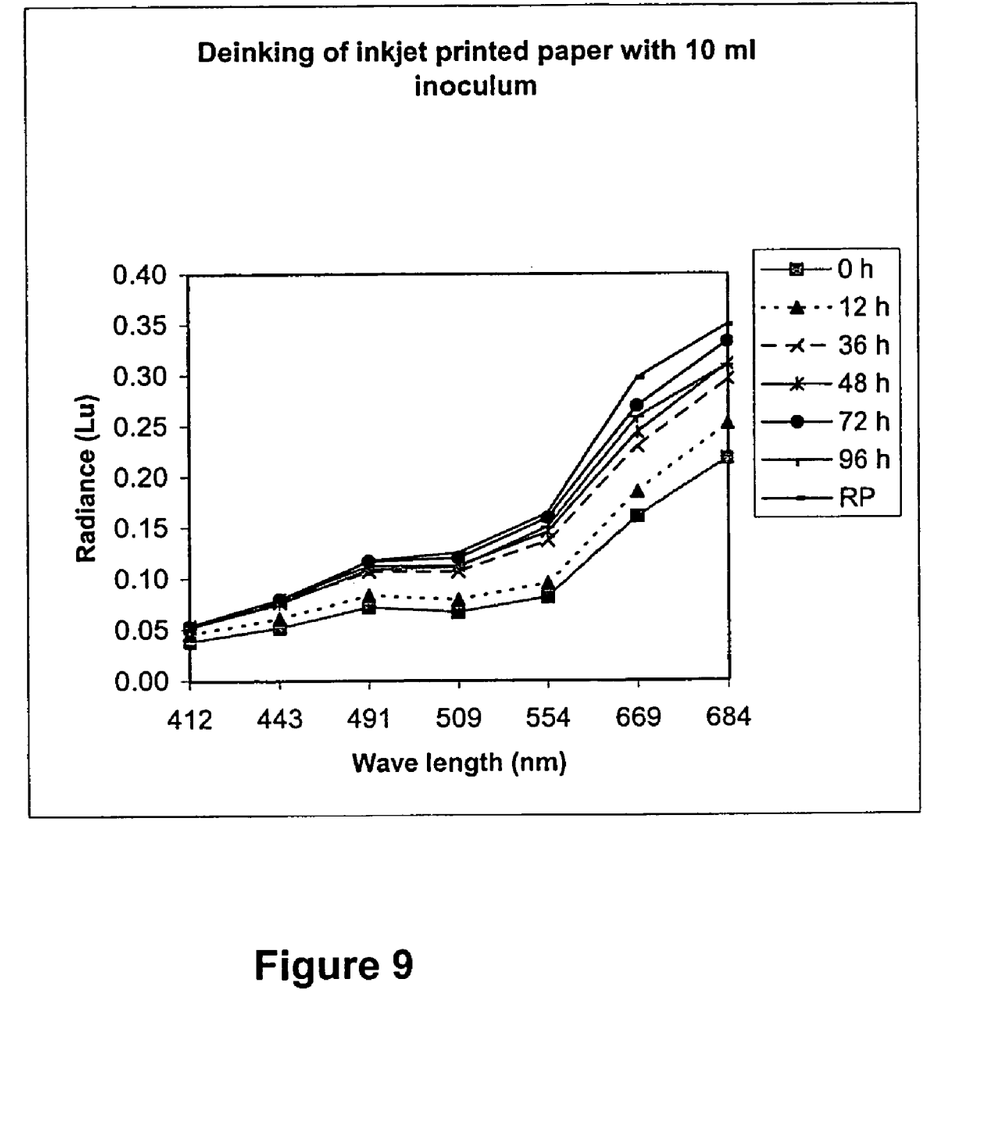
FIG. 9 shows that with an inoculum concentration of 10 ml, maximum brightness is achieved by 72 hours.

FIG. 9 also shows that with an inoculum concentration of 10 ml, maximum brightness is achieved by 72 hours.

What is claimed is:

1. A process for the biological deinking of paper printed with non-impact and non-dispersible ink, the said process comprising:
    (a) growing coccoid bacterial isolate in a nutrient broth containing beef extract, peptic digest of animal tissue in salinated water with salinity ranging from approximately 30 to approximately 35 parts per thousand for at least approximately 4 days;

(b) adding the resulting biomass of step (a) at approximately 20% concentration to inoculate paper pulp diluted to at least approximately 6% consistency suspended in salinated water having a salinity of approximately 15 parts per thousand;

(c) incubating the inoculated pulp for a minimum period of approximately 96 hours followed by diluting the pulp approximately tenfold;

(d) adding approximately 1% by weight of a surfactant and aerating for at least approximately 10 minutes with compressed air to let the stray residual ink particles and contaminants to flow out of the container; and (e) filtering the pulp of step (d) over a funnel under suction, to get a sheet of deinked pulp with uniform thickness and reading its brightness by radiance measurement.

2. A process as claimed in claim 1, wherein in step (a), the bacterium is grown for a minimum of approximately 4 days in nutrient broth containing beef extract and peptic digest of animal tissue in sea water with a salinity in the range of from approximately 30 to 35 approximately parts per thousand.

3. A process as claimed in claim 1, wherein in step (b), the resulting bacterial biomass is concentrated by centrifugation and diluted to get a final optical density of 1.0 measured at 660 nm in a spectrophotometer.

4. A process as claimed in claim 1, wherein the diluted bacterial culture is inoculated to at least approximately 6% pulp suspended in salinated water having a salinity of approximately 15 parts per thousand and incubated for a minimum period of approximately 4 days to completely deink the pulp.

5. A process as claimed in claim 1, wherein the resulting deinked pulp is diluted tenfold, to which approximately 1% surfactant is added, aerated using compressed air, and any free residual ink particles and contaminants are allowed to flow out of the solution.

6. A process as claimed in claim 1, wherein the printed paper is soaked in hot water for approximately 1-2 hours and macerated in the presence of a surfactant to form the paper pulp.

7. A process as claimed in claim 6, wherein the paper is macerated into pulp using a mixer.

8. A process as claimed in claim 1, wherein in step (e), the washed pulp is filtered over a Buchner funnel under suction to get a deinked pulp sheet of uniform thickness.

9. A process as claimed in claim 1, wherein the deinked pulp sheet is pressed at approximately 60° C. for a minimum of approximately 4 hours to make it uniform and dry.

10. A process as claimed in claim 1, wherein the radiance of the resultant deinked sheet is read at wavelengths of from approximately 412 to approximately 684 nm and the radiance expressed as Lux units (LU) {wherein one LU is equivalent to $\mu W/cm^2/nm/Sr$}.

11. A process as claimed in claim 1, wherein the brightness of the resultant deinked sheet is measured as the ratio of radiance of the resultant deinked sheet as compared to the radiance of pulp made out of commercially available recycled paper.

12. A process as claimed in claim 1, wherein in steps (a) and (b), the salinated water is selected from the group of diluted sea water and salinated tap water.

13. A process for biological deinking of paper printed with non-impact and non-dispersible ink, said process comprising:

(a) growing coccoid bacterial isolate (deposited at the Agriculture Research Service Cultural Collection, Illinois, USA with accession No. NRRL B-30638) in a nutrient broth containing beef extract, peptic digest of animal tissue in salinated water with salinity ranging from approximately 30 to approximately 35 parts per thousand for at least approximately 4 days;

(b) adding the resulting biomass of step (a) at approximately 20% concentration to inoculate paper pulp diluted to at least approximately 6% consistency suspended in salinated water having a salinity of approximately 15 parts per thousand;

(c) incubating the inoculated pulp for a minimum period of approximately 96 hours followed by diluting the pulp tenfold;

(d) adding approximately 1% by weight of a surfactant and aerating for at least approximately 10 minutes with compressed air to let the stray residual ink particles and contaminants flow out of the container; and (e) filtering the pulp of step (d) over a funnel under suction, to get a sheet of deinked pulp with uniform thickness and reading the brightness of the pulp sheet by radiance measurement.

14. A process as claimed in claim 13, wherein in step (a), the bacterium is grown for a minimum of approximately 4 days in nutrient broth containing beef extract and peptic digest of animal tissue in sea water with a salinity ranging from approximately 30 to approximately 35 parts per thousand.

15. A process as claimed in claim 13, wherein in step (b), the resulting bacterial biomass is concentrated by centrifugation and diluted to get a final optical density of 1.0 measured at 660 nm in a spectrophotometer.

16. A process as claimed in claim 13, wherein the diluted bacterial culture is inoculated to at least approximately 6% pulp suspended in salinated water having a salinity of approximately 15 parts per thousand and incubated for a minimum period of approximately 4 days to completely deink the pulp.

17. A process as claimed in claim 13, wherein the resulting deinked pulp is diluted tenfold, to which approximately 1% surfactant is added, aerated using compressed air, and any free residual ink particles and contaminants are allowed to flow out of the solution.

18. A process as claimed in claim 13, wherein the printed paper is soaked in hot water for approximately 1-2 hours and macerated in the presence of a surfactant to form the paper pulp.

19. A process as claimed in claim 13, wherein the radiance of the resultant deinked sheet is read at wavelengths of from approximately 412 to approximately 684 nm and the radiance expressed as Lux units (LU) {wherein one LU is equivalent to $\mu W/cm^2/nm/Sr$}.

20. A process as claimed in claim 13, wherein in steps (a) and (b), the salinated water is selected from the group of diluted sea water and salinated tap water.

* * * * *